United States Patent [19]

Parlman et al.

[11] 4,341,715

[45] Jul. 27, 1982

[54] S-ALLYL-S'-N-BUTYL-TRITHIOCARBONATE

[75] Inventors: Robert M. Parlman; James B. Kimble, both of Bartlesville, Okla.

[73] Assignee: Phillips Petroleum Company, Bartlesville, Okla.

[21] Appl. No.: 194,325

[22] Filed: Oct. 6, 1980

[51] Int. Cl.$^3$ .................... B03D 1/02; C07C 154/00
[52] U.S. Cl. .................... 260/455 B; 209/166
[58] Field of Search .................... 260/455 B

[56] References Cited

U.S. PATENT DOCUMENTS

| | | | |
|---|---|---|---|
| 1,659,396 | 2/1928 | Douglass | 260/455 B |
| 2,020,021 | 11/1935 | Farrington et al. | 260/455 B |
| 2,152,461 | 3/1939 | Bishop | 260/455 B |
| 2,574,457 | 11/1951 | Arnold | 260/455 B |
| 2,600,737 | 6/1952 | Crouch et al. | 260/455 B |
| 2,634,291 | 4/1953 | Arnold | 260/455 B |
| 2,858,292 | 10/1958 | Swart et al. | 260/455 B |
| 3,166,580 | 1/1965 | Stanley, Jr. | 260/455 B |
| 3,180,790 | 4/1965 | Goodhue | 260/455 B |

OTHER PUBLICATIONS

Reid, Organic Chemistry of Bivalent Sulfur, vol. IV, Chem. Publishing Co., Inc., New York, N.Y., 1962, p. 178.
Industrial and Engineering Chemistry, vol. 42, No. 5, May, 1950.
Chem. Abstracts, 56:8530i.
Chem. Abstracts, 71:93695j.

*Primary Examiner*—Henry R. Jiles
*Assistant Examiner*—Robert C. Whittenbaugh

[57] ABSTRACT

S-Allyl-S'-n-butyl-trithiocarbonate and S-benzyl-S'-n-butyl-trithiocarbonate, their use and flotation agents and a process to make these novel compositions are disclosed.

1 Claim, No Drawings

S-ALLYL-S'-N-BUTYL-TRITHIOCARBONATE

BACKGROUND OF THE INVENTION

This invention relates to novel chemical compositions, a process to make these compositions and an ore flotation process using these compositions.

Froth flotation is a process for recovering and concentrating minerals from ores. In a froth flotation process, the ore is crushed and wet ground to obtain a pulp. Additives such as mineral flotation or collecting agents, frothing agents, suppressants, stabilizers, etc. are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and the mineral-bearing froth is collected and further processed to obtain the desired minerals. Typical mineral flotation collectors include xanthates, amines, alkyl sulfates, arene sulfonates, dithiocarbamates, dithiophosphates, and thiols.

It is also known from the art that some organic derivatives of trithiocarbonic acid are useful as flotation agents. U.S. Pat. No. 1,659,396, for instance, describes diethyl trithiocarbonate and the production thereof. U.S. Pat. No. 3,166,580 describes dicyclopentyl trithiocarbonates and their production as well as the utility of these compounds as flotation agents.

It is a continuing goal in the ore industry to increase the productivity of ore flotation processes and above all to provide specific processes which are selective to one ore or metal over other ores or metals present in the treated material.

THE INVENTION

Thus, it is one object of this invention to provide new trithiocarbonates.

A further object of this invention is to provide a process to make such trithiocarbonates.

Yet another object of this invention is to provide an ore flotation process wherein such new trithiocarbonates are used as flotation agents.

These and other objects, advantages, details, features and embodiments of this invention will become apparent to those skilled in the art from the following detailed description of the invention and the appended claims.

In accordance with this invention it has now been found that S-allyl-S'-n-butyl trithiocarbonate and S-benzyl-S'-n-butyl trithiocarbonate are both very effective and selective ore flotation agents.

Thus in accordance with a first embodiment of this invention two novel compositions of matter are provided which can be characterized by the formula

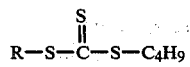

wherein R is allyl or benzyl.

The process for producing these novel compositions of matter differs from the known processes to make dialkyl trithiocarbonates in the use of different starting materials. Thus in accordance with a second embodiment of this invention there is provided a process for producing the above-defined two novel trithiocarbonates. This process comprises (a) reacting an alkali metal hydroxide having the formula

  (I)

wherein M is Li, Na or K with a mercaptan having the formula

  (II)

wherein R is allyl, benzyl or butyl to form

  (III)

(b) reacting R-S-M and $CS_2$ to form

  (IV)

and (c) reacting the product of formula (IV) with a hydrocarbyl halogenide having the formula

  (V)

wherein X is Cl, Br or I and R' is butyl if R is benzyl or allyl and R' is benzyl or allyl if R is butyl, to form a dihydrocarbyl trithiocarbonate having the formula

  (VI)

(c) recovering product (VI) as the product of the process.

The detailed operating conditions for the individual steps are not critical and specific values for the steps can be seen from the following examples. Generally the first step of the reaction, namely the reaction of the mercaptan and the alkali metal hydroxide, is carried out in an aqueous environment and at a temperature of about 25° C. to 100° C. and under a pressure of 0 to 500 psig. The reaction time for this first step is somewhat dependent upon the other reaction conditions but will generally be in the range of 1 to 2 hours.

The second step conditions of this process, namely the reaction of the compound of formula (III) with carbon disulfide are generally in the same ranges as those for the first step.

The reaction of the product of formula (IV) with the hydrocarbyl halogenide will generally be carried out by a slow addition of the two compounds and mixing. The exothermic reaction is generally carried out at a temperature of 25° to 100° C. and at a pressure of 0 to 500 for a time of 1 to 10 hours.

The separation of the dihydrocarbyl trithiocarbonate is carried out by standard techniques.

A further embodiment of this invention resides in an ore flotation process. More specifically the embodiment of this invention resides in a process for separating variable ore materials from gangue materials. The process of this invention distinguishes over the known processes primarily in the new of a new flotation agent to be defined. Otherwise the recovery process involves crushing of the ore and ore grinding to obtain a pulp. In this pulp the flotation agent is incorporated and the pulp is aerated to produce a froth at the surface which is rich in valuable ore materials but depleted of the gangue materials. The ore materials, optionally, after additional flotation and frothing steps are recovered. Frothing agents, selective suppressants and stabilizers that are well known in the art can be used in the various steps.

The trithiocarbonates useful in the ore flotation process of this invention are characterized by the formula

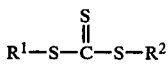

wherein $R^1$ is a hydrocarbyl radical having 1 to 20 carbon atoms and $R^2$ is an alkenyl radical having 2 to 12 carbon atoms or an aryl substituted methyl radical having 7 to 12 carbon atoms. Examples of the dihydrocarbyl trithiocarbonates used as the flotation agent in the process of this invention are S-allyl-S'-methyl trithiocarbonate
S-allyl-S'-ethyl trithiocarbonate
S-allyl-S'-butyl trithiocarbonate
S-allyl-S'-hexyl trithiocarbonate
S-allyl-S'-octyl trithiocarbonate
S-allyl-S'-dodecyl trithiocarbonate
S-allyl-S'-eicosyl trithiocarbonate
S-allyl-S'-cyclohexyl trithiocarbonate
S-2-butenyl-S'-butyl trithiocarbonate
S-3-butenyl-S'-butyl trithiocarbonate
S-2-hexenyl-S'-butyl trithiocarbonate
S-2-dodecenyl-S'-butyl trithiocarbonate
S-benzyl-S'-butyl trithiocarbonate
S,S'-diallyl trithiocarbonate
S-allyl-S'-butenyl trithiocarbonate Hereinafter, the designation S and S' in the nomenclature is omitted for convenience but it is understood that the trithiocarbonates herein disclosed are those having the S- and S'- substitution.

The preferred compositions used as the flotation agent in the process of this invention are allyl n-butyl trithiocarbonate and benzyl n-butyl trithiocarbonate.

The amount of the dihydrocarbyl trithiocarbonate used in the process of this invention is not critical. The quantity will depend upon other process parameters. Generally, the amount of the dihydrocarbyl trithiocarbonate used will be in the range of about 0.001 lbs to 1.0 lbs of the dihydrocarbyl trithiocarbonate per ton of ore. Preferably the collector or flotation agent will be used in a quantity of about 0.01 to 0.10 lbs/ton.

Metal-Bearing Ores

It is generally believed that the trithiocarbonates disclosed herein are useful for separating any valuable metal from its corresponding gangue material. It is also understood that the trithiocarbonates may separate a mixture of metals that are contained in a particular mining deposit or ore, said mixture being further separated by subsequent froth flotations or any other conventional separating methods. The trithiocarbonates herein disclosed are particularly useful for separating molybdenum minerals from the total ore. Such molybdenum bearing ores are for example, but not limited to, such materials as

| Molybdenum-Bearing ores: | |
|---|---|
| Molybdenite | $MoS_2$ |
| Wulfenite | $PbMoO_4$ |
| Powellite | $Ca(Mo,W)O_4$ |

| -continued | |
|---|---|
| Molybdenum-Bearing ores: | |
| Ferrimolybdite | $Fe_2Mo_3O_{12}.8H_2O$ |

Other metal bearing ores within the scope of this invention are, for example, but not limited to, such materials as

| Copper-Bearing ores: | |
|---|---|
| Covallite | $CuS$ |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_3SbS_2$ |
| Tennanite | $Cu_{12}As_4S_{13}$ |
| Cuprite | $Cu_2O$ |
| Tenorite | $CuO$ |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_8$ |
| Famatinite | $Cu_3(Sb,As)S_4$ |
| Bournonite | $PbCuSbS_3$ |
| Lead-Bearing ore: | |
| Galena | $PbS$ |
| Antimony-Bearing ore: | |
| Stilnite | $Sb_2S_4$ |
| Zinc-Bearing ores: | |
| Sphalerite | $ZnS$ |
| Zincite | $ZnO$ |
| Smithsonite | $ZnCO_3$ |
| Silver-Bearing ores: | |
| Argentite | $Ag_2S$ |
| Stephanite | $Ag_5SbS_4$ |
| Hessite | $AgTe_2$ |
| Chromium-Bearing ores: | |
| Daubreelite | $FeSCrS_3$ |
| Chromite | $FeO.Cr_2O_3$ |
| Gold-Bearing ores: | |
| Sylvanite | $AuAgTe_2$ |
| Calaverite | $AuTe$ |
| Platinum-Bearing ores: | |
| Cooperite | $Pt(AsS)_2$ |
| Sperrylite | $PtAs_2$ |
| Uranium-Bearing ores: | |
| Pitchblende | $U_2O_5(U_3O_8)$ |
| Gummite | $UO_3.nH_2O$ |

The presently preferred ores in connection with which the process of this invention is applied are molybdenum, copper and iron ores or minerals.

Separation Conditions

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of the inventive compound allyl n-butyl trithiocarbonate. 150 Milliliters of distilled water and 44 grams (1.1 moles) of sodium hydroxide were added to a three-necked flask fitted with an additional funnel, stirrer and reflux condenser. After the base had dissolved and the solution cooled to about ambient room temperature, 90 grams (1.0 moles) of n-butyl mercaptan was added and the mixture was stirred for 1 hour at room temperature, whereupon 100 grams (1.33 moles) of carbon disulfide was added. The mixture was stirred for another hour. Within 1 hour 85 grams (1.1 moles) of allyl chloride was slowly added to this stirred mixture. The reaction was exothermic at this point. The mixture was stirred until the heat dissipated whereupon two liquid layers formed. The lower orange oily layer was separated, heated at 90°–100° C./17 mm Hg on a rotary evaporator to remove unreacted starting material to give 202 grams of product which are analyzed by Mass Spectroscopy and NMR and found to be consistent with the allyl n-butyl trithiocarbonate solution. In addition, elemental analysis for $C_8H_{14}S_3$ was:

|  | Calculated | Found |
| --- | --- | --- |
| percent C | 46.55 | 46.20 |
| percent H | 6.83 | 6.80 |
| percent S | 46.61 | 49.0 |

EXAMPLE II

This example describes the preparation of the inventive compound benzyl n-butyl trithiocarbonate. The procedure described in Example I was repeated except 127 grams (1 mole) of benzyl chloride was used instead of allyl chloride. There was obtained 227.9 grams of product analyzed by Mass Spectroscopy, NMR, and Carbon-13 NMR and found to be consistent with the benzyl n-butyl trithiocarbonate structure. In addition, elemental analysis for $C_{12}H_{16}S_3$ were:

|  | Calculated | Found |
| --- | --- | --- |
| percent C | 56.20 | 57.4 |
| percent H | 6.29 | 6.1 |
| percent S | 37.51 | 34.7 |

The product was found by Mass analysis to be a mixture of 82 wt.% benzyl n-butyl trithiocarbonate, 11 wt.% benzyl thioformate and 7 wt.% unreacted benzyl chloride. Elemental analysis for this 82/11/7 wt.% mixture was calculated as:

|  | Calculated | Found |
| --- | --- | --- |
| percent C | 57.0 | 57.4 |
| percent H | 6.1 | 6.1 |
| percent S | 34.9 | 34.7 |
| percent Cl | 2.0 | — |

EXAMPLE III

This example illustrates the use of the inventive compounds as ore flotation agents using the Hallimond cell. Reasonably pure mineral sulfides were employed so that more accurate measurements could be made without interference from other materials such as gangue or nonsulfide ores, etc. Other similar ore flotation agents are also tested as controls. The following is a typical procedure. To a 70 milliliter capacity Hallimond cell was charged 1 gram of granulated chalcocite ($Cu_2S$) and about 69 milliliters of demineralized water (pH=6.5, resistivity>1 million $\Omega$cm) and enough 10 wt.% aqueous NaOH to maintain the pH at 9.04. The mineral was conditioned in the cup for 5 minutes while magnetic agitation was applied and maintained constant by a magnetic field, revolving at 800 rpm. A flow of nitrogen, measured by a calibrated capillary (F and P Co., Precision Bore Flowrator Tube No. 08F-1/16-08-5/36) was also maintained constant at 4 cfs. A volume of 100 milliliters of demineralized water adjusted to a pH of 9.04 with 10 wt.% aqueous NaOH was then introduced into the cell. Flotation was maintained for 10 minutes using the same value of nitrogen flow, 4 cPs, but 700 rpm agitation; the pH remained unchanged. The floated fractions were recovered, oven dried at 82° C. (180° F.) for 24 hours and weighed. There was obtained 0.04 grams of chalcocite (4 wt.%) illustrating the inability of the mineral to float by itself. The material remaining in the Hallimond cell, referred herein as "sink" or "reject", was assumed without weighing to be the balance, namely, 0.96 grams (96 wt.%). The run was then repeated several times except each time a different flotation agent was added along with the ore. Potassium amyl xanthate, KAX, is a known commercial flotation agent for copper and was used as a control. The sodium salts of allyl trithiocarbonate and butyl trithiocarbonate are also known to act as flotation agents and were used as controls. The results which are listed in Table I show the inventive compounds benzyl n-butyl trithiocarbonate and allyl n-butyl trithiocarbonate to be useful as ore flotation agents for copper-bearing ores such as chalcocite and chalcopyrite. The results show the inventive compounds are useful in floating other sulfide ores such as galena and sphalerite.

TABLE I

| Mineral | Flotation Agent Collector | mg/Liter | pH | Wt. % Floats | Wt. % Sinks |
| --- | --- | --- | --- | --- | --- |
| 1. Chalcocite, $Cu_2S$ | None | — | 9.04 | 4 | 96 |
|  | Potassium Amyl Xanthate | 5 | 9.0 | 96 | 4 |
|  | Na Salt of n-Butyl Trithiocarbonate | 5 | 9.0 | 100 | 0 |
|  | Na Salt of Allyl Trithiocarbonate | 5 | 9.1 | 82 | 18 |
|  | Allyl n-Butyl Trithiocarbonate | 5 | 9.1 | 96 | 4 |
|  | Benzyl n-Butyl Trithiocarbonate | 5 | 9.0 | 98 | 2 |
| 2. Chalcopyrite, $CuFeS_2$ | None | — | 9.01 | 4 | 96 |
|  | Potassium Amyl Xanthate | 5 | 9.03 | 48 | 52 |
|  | Na Salt of n-Butyl Trithiocarbonate | 5 | 9.09 | 72 | 28 |
|  | Na Salt of Allyl Trithiocarbonate | 5 | 8.8 | 93 | 7 |

TABLE I-continued

| | Hallimond Cell Ore Flotation | | | | |
|---|---|---|---|---|---|
| | Flotation Agent | | | Wt. % | |
| Mineral | Collector | mg/ Liter | pH | Floats | Sinks |
| | Allyl n-Butyl Trithiocarbonate | 5 | 9.0 | 89 | 11 |
| | Benzyl n-Butyl Trithiocarbonate | 5 | 9.0 | 96 | 4 |
| 3. Galena, PbS | Allyl n-Butyl Trithiocarbonate | 7.5 | 8.1 | 43 | 57 |
| | Benzyl n-Butyl Trithiocarbonate | 7.5 | 8.4 | 50 | 50 |
| 4. Sphalerite, ZnS | Allyl n-Butyl Trithiocarbonate | 7.5 | 9.1 | 62 | 38 |
| | Benzyl n-Butyl Trithiocarbonate | 7.5 | 9.1 | 70 | 30 |

EXAMPLE IV

This example illustrates the use of allyl n-butyl trithiocarbonate as an ore flotation agent, particularly for the recovery of molybdenum. A sulfide ore primarily of chalcocite, $Cu_2S$, and molybdenite, $MoS_2$, in a gangue of quartz, orthoclase, albite, and clay minerals with an assay approximately 1.00 wt.% total Cu, 0.25 wt.% acid soluble Cu, and 0.015 wt.% Mo was used in this example. A standard laboratory batch flotation test was conducted by grinding a 1000 gram sample of the above ore in a lab rod ball mill along with enough water to make a 75 wt.% slurry and enough lime to obtain a pH of 11.5. To this mixture were added 0.005 lbs/ton sodium isopropyl xanthate and 0.01 lbs/ton allyl ester of amyl xanthate (AC 3302 from American Cyanamid). The grinding was such that the particle size was 25%+65 mesh and 49%−200 mesh as measured by U.S. Standard screen size. The ground sample was then transferred to a Denver laboratory flotation cell and diluted with water to 35 wt.% solids. To this mixture was added 0.05 lb/ton of a frother agent Dowfroth 250 (a polyoxypropylene glycol monomethyl ether, Mol. wt. 250 from Dow Chemical Co.) and the mixture conditioned for one minute. The mixture was then floated for 4 mins. at 800 rpm pulling all around the cell once every 10 seconds. After 4 mins. of flotation, 0.005 lb/ton of a flotation agent was added and flotation was continued for another 4 mins. The combined floats were then dried and analyzed. Table II lists the results of two runs, one where a standard flotation agent namely allyl ester of amyl xanthate (3302 from American Cyanamid) was employed as a control and another wherein the inventive compound, allyl n-butyl trithiocarbonate, was used. These results indicate the inventive compound significantly increases the recovery of molybdenum, the recovery of other metals such as copper and iron is also increased by the use of the compounds of this invention as compared to the chemically closed related xanthate compound.

TABLE II

Ore Flotation - Effect of Collector Type on Molybdenum Recovery (Chalcocite-Molybdenite Ore)

| | Av. Wt. % Recovery[a] | | |
|---|---|---|---|
| Collector (0.01 lbs/ton) | Cu | Mo | Fe |
| Control-Allyl Amyl Xanthate | 81.9 | 44.3 | 36.7 |
| Invention-Allyl n-Butyl Trithiocarbonate | 82.5 | 52.6 | 38.3 |

[a]Based on the amount of metal available in original ore. Obtained as the sulfide. Average based on triplicate runs.

EXAMPLE V

This example illustrates the use of allyl n-butyl trithiocarbonate as an ore flotation agent, particularly for the recovery of molybdenum, using another type of ore and flotation process then that described in Example IV. The ore used in this example was primarily of chalcopyrite, $CuFeS_2$, and molybdenite, $MoS_2$ and assayed at 0.035 wt.% Mo. A standard laboratory batch flotation test was conducted by grinding a 2000 gram sample of the above ore (preground to just passing 10 mesh) in a lab ball mill with 860 milliliters of hot (100° F.) tap water and enough lime (about 2 grams) to bring the pH to 10.2. Normal grind time was 13.5 mins. giving a particular size distribution of 10.9%+65 mesh and 52.6 passing −200 mesh. After 6.5 mins. of grind time 0.01 lbs/ton of a primary collector was added, either SM-8 (xanthogen formate from the Minerec Co.) or the inventive compound allyl n-butyl trithiocarbonate along with 0.0154 lbs/ton sodium isopropyl xanthate (a secondary collector Z-11 from Dow Chemical Co.) and 0.029 lbs/ton of a frothing agent (Shell 1639). The charge was ground for an additional 7 mins. The ball mill was opened, 1000 milliliters of hot tap water added and the contents ground for 15 seconds to facilitate handling whereupon the charge was transferred to a Denver flotation cell. Additional hot water (100° F.) was added to dilute the solids to about 20 wt.%. The agitator was turned on at 1200 rpm and the pulp allowed to condition for 2 minutes. Air was introduced into the pulp through the agitator at 42.5 cfs. The concentrate was scraped off with a paddle at 50 strokes/min. for the 2 minute float period. The air and agitator were turned off whereupon 0.0016 lbs/ton of a secondary collector (Z-11) was added plus 0.0174 lbs/ton frothing agent (Shell 1639) and 250 grams of hot water. The agitator was turned on at 1200 rpm, the pulp conditioned for 1 min. and air again introduced at 42.5 cfs. and the concentrate scraped off a 50 strokes a minute for the 2 minute float. The air and agitator were again turned off, whereupon 0.0008 lbs/ton Z-11 collector, 0.0087 lbs/ton Shell 1639 frother, and 250 grams of hot water added. The agitator was turned on at 1200 rpm and the pulp again conditioned for 2 minutes. Air was then introduced at 42.5 cfs and the concentrate scraped off at 50 strokes/minute for a 2 minute float. In this way, three floats were obtained which were combined, dried and analyzed. Table III lists the results from two runs having 3 floats in each run wherein during the ball milling steps before the first flotation there was added in the first run the control collector xanthogen formate (SM-8) and in the second run the inventive collector allyl n-butyl trithiocarbonate. These results indicate the inventive compound allyl n-butyl trithiocarbonate to be a good ore flotation agent, particularly when used to recover molybdenum.

TABLE III

Ore Flotation - Effect of Collector Type on Molybdenum Recovery (Chalcopyrite-Molybdenite Ore)

| Primary Collector | Av. Wt. % Cu | Mo |
|---|---|---|
| Control-Xanthogen Formate | 84.94 | 91.37 |
| Invention-Allyl n-Butyl Trithiocarbonate | 85.08 | 93.20 |

*a*Based on the amount of metal available in original ore. Obtained as the sulfide. Average based on triplicate runs.

SUMMARY

In summary, the data herein disclosed reveals two new compounds, namely, S-allyl-S'-n-butyl trithiocarbonate and S-benzyl-S'-butyl trithiocarbonate which are useful as ore flotation agents. Both compounds are particularly suited for floating copper sulfides and S-allyl-S'-n-butyl trithiocarbonate is especially suited for floating molybdenum sulfide.

Reasonable variations and modifications which will become apparent to those skilled in the art can be made in this invention without departing from the spirit and scope thereof.

We claim:
1. S-Allyl-S'-n-butyltrithiocarbonate.

* * * * *